United States Patent [19]

Marks

[11] Patent Number: 5,225,329
[45] Date of Patent: Jul. 6, 1993

[54] METHOD FOR EARLY DETECTION OF INTESTINAL ISCHEMIA

[75] Inventor: William H. Marks, Woodbridge, Conn.

[73] Assignee: Yale University, New Haven, Conn.

[21] Appl. No.: 780,736

[22] Filed: Oct. 18, 1991

[51] Int. Cl.$^5$ .................. G01N 33/53; C12Q 1/00
[52] U.S. Cl. .................... 435/7.9; 435/188; 435/968; 436/518; 436/811; 436/815; 436/804
[58] Field of Search .............. 435/7.9, 188, 968; 436/804, 811, 815, 518

[56] References Cited

PUBLICATIONS

Alpers, D. H., et al., Proc. Natl. Acad. Sci. USA 81: 313–317 (1984).
Ausubel, F. M., et al., eds., Current Protocols In Molecular Biology, John Wiley, New York, 1990 Unit 11.2.2.
Bass, N. M., and Manning J. A., Biochem. Biophys. Res. Commun. 137: 929–935 (1986).
Bradford, M. M., Anal. Biochem. 72: 248–254 (1976).
Dempsey, M. E., et al., Chem. Phys. Lipids 38: 223–237 (9185).
Gordon, J. L., et al. Chem. Phys. Lipids 38: 137–158 (1985).
Grendell, J. H., §106 in Cecil's Textbook of Medicine, 18th ed., W. B. Saunders Co., Harcourt Brace Jovanovich, Philadelphia, 1988, pp. 760–765.
Lobe, T. E., et al., J. Ped. Surg. 18: 449–452 (1983).
Ockner; R. K., and Manning, A., J. Clin. Invest. 54: 326–338 (1974).
Ockner, R. K., et al., J. Biol. Chem. 257: 7872–7878 (1982).
Sacchettini, J. C., et al., J. Biol. Chem. 263: 5815–5819 (1988).
Sacchettini, J. C., et al., Molec. Cell. Biochem. 98: 81–93 (1990).
Said, B., and Schulz, J. Biol. Chem. 259: 1155–1159 (1984).
Sweetser, D. A., et al., J. Biol. Chem. 262: 16060–16071 (1987).
Varley's Practical Clinical Biochemistry, 6th ed., CRC Press, 1988, pp. 112–113.
Crisman, T. S. et al "Measurement of Rat Heart Fatty Acid Binding Protein by ELISA . . . " 1987 J. Mol. Cell Cardiol. 19: 423–431.
Catty, D. *Antibodies Volume I A Practical Approach* 1988 IRL Press Ltd., Oxford, England.

*Primary Examiner*—Esther L. Kepplinger
*Assistant Examiner*—Nancy J. Parsons
*Attorney, Agent, or Firm*—St. Onge Steward Johnston & Reens

[57] ABSTRACT

Disclosed is a method for the screening of pathological condition in the intestinal tract of an animal or a human being, e.g., intestinal ischemia, necrotizing enterocolitis, inflammatory bowel disease and bowel graft rejection. The method assays elevated levels of lipid binding protein, more particularly intestinal fatty acid binding protein, in a biological sample obtained from the animal or human being. Serum or urine are preferred biological samples. Preferred methods employ an immunological assay such as a radioimmunoassay or an enzyme-linked immunosorbent assay for the detection of intestinal fatty acid binding proteins in the sample.

20 Claims, 3 Drawing Sheets

METHOD FOR EARLY DETECTION OF INTESTINAL ISCHEMIA

BACKGROUND OF THE INVENTION

This invention relates to a method for the diagnosis of pathological processes in vertebrate intestinal tracts.

Acute and chronic intestinal ischemic syndromes are difficult to diagnose in early, reversible stages. Gradual occlusion of the intestinal blood supply may be asymptomatic because of the development of adequate collateral circulation. However, when intestinal blood flow falls below a critical level, ischemic necrosis of the supplied areas results, presenting signs that are often virtually identical with other intra-abdominal conditions. (For a general discussion, see Grendell, J. H., §106 in *Cecil's Textbook of Medicine*. 18th ed., W. B. Saunders Co., Harcourt Brace Jovanovich, Philadelphia, 1988, pp. 760–765.)

Several serum markers for ischemic injury have been proposed, including phosphate (ibid., p. 762) and hexosaminidase (Lobe, T. E., et al., *J. Ped. Surg.* 18: 449–452 (1983)). However, these lack sensitivity, rising only with full-thickness necrosis. These methods also lack specificity and adequate sensitivity for early detection of ischemia. More commonly employed diagnostic tools include extensive radiographic studies, especially angiography, and exploratory surgery (Grendell, cited above).

SUMMARY OF THE INVENTION

It is an object of the present invention to provide a method for the early diagnosis of pathological processes such as intestinal ischemia, necrotizing enterocolitis, inflammatory bowel disease and bowel graft rejection in the intestinal tracts of animals and human beings. It is another object of the invention to provide a diagnostic method that is simple, sensitive, noninvasive, and economical. It is a further object of this invention to provide an assay for the detection of intestinal fatty acid binding protein in biological samples such as serum, urine, and tissue homogenates.

These and other objects are achieved by the present invention which describes a method for the diagnosis of intestinal ischemia and similar syndromes involving intestinal pathology. The method of this invention involves an assay for the quantitation of lipid binding protein, particularly intestinal fatty acid binding protein, in biological fluid samples such as serum, urine, and tissue homogenates taken from animals or human beings. Serum and urine are preferred samples. Preferred methods employ an immunological assay such as a radioimmunoassay or an enzyme-linked immunosorbent assay for the quantitative determination of binding protein.

In the practice of the invention, the method involves obtaining a biological sample from an animal or human being, determining the level of lipid binding protein, notably intestinal fatty acid binding protein, in the sample, and comparing said determined level to the level in a normal animal or human being.

In a most preferred embodiment, intestinal fatty acid binding protein is detected in sample urine or serum using an antibody to rat intestinal fatty acid binding protein, particularly recombinant rat intestinal fatty acid binding protein, in a radioimmunoassay.

DETAILED DESCRIPTION OF THE INVENTION

Figure 1:
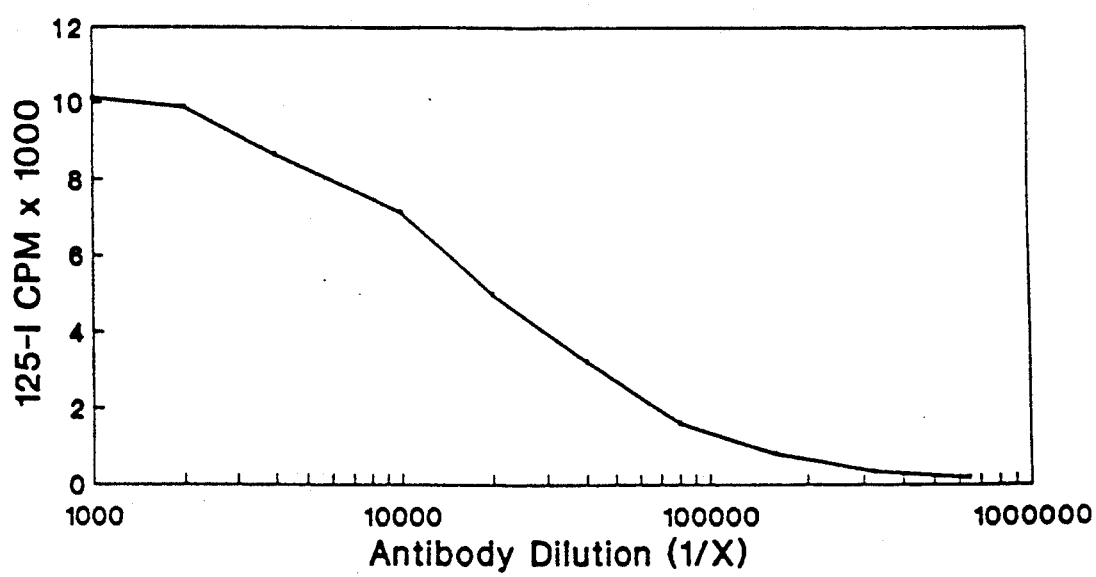
FIG. 1 is a titration curve of rabbit anti-intestinal fatty acid binding protein. A 2:1 dilution (v/v) series of rabbit anti-intestinal fatty acid binding protein antiserum is tested against radiolabelled intestinal fatty acid binding protein (hereinafter referred to as I-FABP, 17,500 cpm/100 ul). At a 1:8000 (v/v) dilution of antiserum, 60% of the label could be precipitated.

This invention describes methods for diagnosing pathological processes in the intestinal tracts of animals and human beings. The methods employ assays for lipid binding protein, notably intestinal fatty acid binding protein, in biological samples such as urine and serum.

Fatty acid binding proteins are a group of relatively abundant, small polypeptides that have about 127 to 132 amino acids (with molecular weights of about 12,000 to about 15,000) and belong to a family of related lipid binding proteins that bind hydrophobic ligands including retinoids. Fatty acid binding proteins have been identified and isolated from a number of tissues, including the intestine, the liver, and the heart. Their distinct structures and patterns of tissue-specific and developmental expression suggest they may have a variety of functions, with proposed physiologic roles suggested to be the facilitation of the uptake of long chain fatty acids into cells and transport to organelles or metabolic pathways, and the protection of cell membranes and enzymes from potentially toxic, detergent effects of high concentrations of fatty acids and their acyl-CoA derivatives (Sacchettini, J. C., et al., *J. Biol. Chem.* 263:5815–5819 (1988)).

Intestinal fatty acid binding protein contains a single ligand binding site that binds long chain $C_{16}$ to $C_{20}$ fatty acids (ibid.). Analogous proteins have been identified in a number of animals, including the rat, the chicken and man. The protein is well-conserved between species, having an inter-species homology of over 80% (ibid.). In mammals, the protein is reported to constitute about 2% of the intestinal mucosal protein and to be present primarily in the tips of the intestinal villi (Ockner, R. K., and Manning, A., *J. Clin. Invest.* 54:326-338(1974)).

Intestinal fatty acid binding protein (hereafter referred to as I-FABP) is a cytosolic protein that has not, under normal conditions, been heretofore reported to be found in serum (Bass, N. M., and Manning, J. A., *Biochem. Biophys. Res. Commun.* 137: 929-935(1986)). However, liver fatty acid binding protein, another member of the lipid binding protein family, has been identified in serum (Dempsey, M. E., et al., *Chem. Phys. Lipids* 38: 223-237 (1985)).

This invention is based upon the finding that lipid binding protein, notably I-FABP, can be used as a marker for early mesenteric ischemia at a stage when tissue salvage is still possible. In our experiments, I-FABP rose significantly in both the serum and urine of rats with moderate ischemic damage of the intestinal mucosa.

In the practice of this invention, pathological processes of the intestinal tract, such as intestinal ischemia, necrotizing enterocoloitis, inflammatory bowel disease, and bowel graft rejection, are diagnosed in animals and in human beings by assaying for elevated levels of lipid binding protein, notably intestinal fatty acid binding protein, in biological samples obtained from the animals or human beings. Typical biological samples include, but are not limited to, serum, urine, or tissue homogenates prepared, for example, from intestinal biopsies. Preferred samples are serum and urine. Serum is particularly preferred.

A biological sample is obtained from an animal or a human being. The level of lipid binding protein, notably intestinal fatty acid binding protein, is then determined in the sample, and this level is compared to the level obtained in a sample from a normal animal or human being.

Biological samples such as serum or urine from animals or human beings may be assayed for lipid binding protein, particularly I-FABP, using any analytical method for the proteins such as, for example, chemical or bioassays. Sensitive and specific assays, for example, include immunoassays such as radioimmunoassays or enzymeimmunoassays employing polyclonal or monoclonal antibodies to I-FABP.

By "antibody" is meant an immunoglobulin having a specific amino acid sequence by virtue of which it interacts with a I-FABP antigen that induced its synthesis in cells of the lymphoid series, or with an antigen closely related to it. Any I-FABP antibody may be employed in the assays of this invention.

Antibodies to lipid binding proteins such as I-FABP are generated using conventional techniques (summarized in *Varley's Practical Clinical Biochemistry*, 6th ed., CRC Press, 1988, pp. 112-113). Polyclonal antibodies, for example, are obtained by immunizing intramuscularly, subcutaneously, or intradermally, a rabbit, a guinea pig or a sheep with I-FABP, reimmunizing with a booster, and harvesting antibody-containing sera in about 7 to 14 days. Monoclonal antibodies, for example, are obtained by immunizing mice with I-FABP, testing for antibody content, hybridizing or fusing spleen cells from an immunized mouse with a plasmacytoma cell line in the presence of polyethylene glycol, culturing the fused cell types so produced, and selecting an appropriate clone. Polyclonal antibodies to lipid binding proteins in rabbits have been described (see, for example, Ockner, R. K., et al., *J. Biol. Chem.* 257:7872-7878 (1982) and Okner and Manning, cited above), and an example is given in the next section.

Fatty acid binding protein used as an antigen for antibody production can be a natural form isolated from tissues or a recombinant form expressed in a transformed or transfected microbiological or other cell line. The isolation of rat I-FABP, for example, has been described (ibid.), as have isolations of heart and liver FABPs (Said, B., and Schulz, *J Biol. Chem.* 259:1155-1159 (1984)). The complete sequence of the highly conserved analogous human I-FABP has been determined (Sweetser, D. A., et al., *J. Biol. Chem.* 262:16060-16071 (1987)) and has been deposited in the GenBank TM/EMBL Data Bank (Accession No. J03465). Preparative schemes are laborious, however, and yield low to modest amounts of protein.

To obtain large quantities, expression of a recombinant form is preferred. Cloned cDNAs encoding several fatty acid binding proteins, including heart and intestinal FABs, have been previously described (see, for example, Alpers, D. H., et al., *Proc. Natl. Acad. Sci. USA* 81:313-317 (1984) describing cloning and the complete amino acid sequence of rat I-FABP). A number of other preparative procedures for recombinant I-FABP production in *E. coli* have been described, including insertion of a rat I-FABP cDNA into a prokaryotic expression vector containing a leftward promoter from phage lambda (pL) and temperature induction of the promoter in a host strain containing a thermolabile repressor; more recently, insertion using a pMON vector is induced without temperature restrictions by adding nalidixic acid to the culture (see Sacchettini, J. C., et al., *Molec. Cell. Biochem.*, 98:81-93 (1990) and the references cited therein).

It is an advantage of the present invention that a number of natural and recombinant lipid binding proteins, especially I-FABP, are available for use for intestinal pathology assays. It is a further advantage of the invention that these markers are small, soluble proteins that can be conveniently employed in assays.

To assay for lipid binding protein, notably I-FABP, one embodiment employs an enzyme-linked immunosorbent assay (ELISA, described in Ausubel, F. M., et al., eds., *Current Protocols in Molecular Biology*, John Wiley, New York, 1990, Unit 11.2.2). ELISAs typically utilize an enzyme such as horseradish peroxidase, urease, or alkaline phosphatase conjugated to the anti-I-FABP antibody or conjugated with a tag that interacts with a correspondingly tagged antibody. Example tags, where employed, are avidin and biotin. Test serum is incubated in the wells of microtiter plates with conjugated antibody. If the serum contains I-FABP antigen, the conjugated antibodies adhere to it. Subsequent measurement of enzyme activity estimates how much tagged antibody is present and bound to I-FABP. From that, amounts of I-FABP in the original test sample is calculated. Preferred ELISAs employ substrates known to those skilled in the art to be easily measurable, for example, by viewing color development in comparison with standards or by employing a spectrophotometer.

Most preferred substrates are chromophoric or yield chromophoric products, so that enzyme activity can be readily measured by the appearance or disappearance of color. Examples of enzyme substrates include p-nitrophenyl phosphate for alkaline phosphatase, bromocresol purple and urea for urease, p-nitrophenyl-beta-galactopyranoside for beta-galactosidase, and the like.

Horseradish peroxidase requires hydrogen peroxide in addition to another substrate that serves as a hydrogen donor including, for example, 2,2'-azino-bis(3-ethylbenzthiazoline-6-sulfonic acid) (ABTS), 5-aminosalicylic acid, o-diaminobenzidine, 3,3'-dimethoxybenzidine, o-phenylenediamine (free base or dihydrochloride), 3,3',5,5'-tetramethylbenzidine (base or dihydrochloride), and the like chromogens. An alternate embodiment employs a radioimmunoassay (RIA, described in Ausubel, cited above, at §11.16.1). Typical RIAs employ antigens radiolabelled with $^{125}$I, $^{3}$H or other isotope that can be easily detected. For example, $^{125}$I-labelled I-FABP can be employed. Antibody is titrated with labelled antigen, and the activity and sensitivity of the antiserum is determined. A dilution series of samples to which known amounts of antigen have been added are distributed in wells of microtiter plates. Antibody is added, the well material and/or the supernatants analyzed for radioactivity after incubation and compared to a standard curve prepared using pure antigen. Amounts of unlabelled antigen bound are calculated by difference. These and other variations on RIA protocols known by those skilled in the art are encompassed by this invention, and an example direct RIA for I-FASB is detailed hereinafter.

Samples for analysis using the method of this invention, e.g., serum, can contain lipid. Lipid-containing samples may be delipidated prior to assay. Any water-immiscible solvent system that solubilizes the lipid can be employed in the delipidation, such as, for example, butanol and/or ether. However, delipidation of serum samples may increase background lipid binding protein levels; with I-FABP, for example, delipidation results in measurable, albeit low, normal I-FABP levels. Therefore, serum delipidation is not preferred in assays for I-FABP.

Lipid binding proteins, particularly the liver and intestinal FABPs, do not occur uniformly along the intestinal tract. On the contrary, there are gradients of lipid binding protein concentrations in the various tissues. For example, the concentration of I-FABP is considerably lower in the colon than in the small intestine, and distribution in the duodenum, jejunum, and ileum is not uniform. Liver FABP and ileal lipid binding protein are present in the intestine. It is an advantage of the present invention, therefore, that specific and sensitive immunoassays for the detection of various lipid binding proteins, including I-FABP, and the patterns of their distribution can provide not only an indication of ongoing pathological processes in the overall intestinal tract, but also differential diagnoses of pathological processes involving specific areas.

This invention provides novel diagnostic methods employing biochemical markers for early mesenteric ischemia, necrotizing enterocolitis, rejection of small bowel allografts, and the like pathologic conditions affecting intestinal mucosa.

EXAMPLES

The following examples are presented to further illustrate and explain the present invention and should not be taken as limiting in any regard. Unless otherwise indicated, all parts and percentages are by weight, and are based on the weight at the particular stage of the processing being described. Values for fluid and tissue levels of immunoreactive I-FABP are expressed as mean±standard error of the mean.

EXAMPLE 1

This example describes a radioimmunoassay for the quantitation of intestinal fatty acid binding protein in rat serum, urine or tissue. The assay is sensitive for immunoreactive I-FABP in concentrations between about 4 and about 125 ng/ml.

I-FABP preparation. Purified, recombinant rat I-FABP is prepared in a straightforward manner in high yield as previously described using a pMON-I-FABP expression vector to direct synthesis of I-FABP in *E. coli* strain JM101, A.T.C.C. No. 33876 (Sacchettini, J. C., et al., *Molec. Cell. Biochem.*, cited above). Briefly summarized, rat I-FABP cDNA is placed just downstream of a translational enhancer element from bacteriophage teriophage T7, and transcription, controlled by a recA promoter, can be readily induced by adding nalidixic acid to the culture after the cells have reached a desired density. After harvest, the cells are pressed and subjected to osmotic shock to lyse them. Soluble proteins obtained in the supernatant are dialyzed, subjected to ultrafiltration through a membrane and then gel filtered on Sephadex TM -G50. Three to four mg purified I-FABP per liter culture are obtained.

Radiolabelling. Five micrograms of rat I-FABP in 0.05M sodium phosphate buffer, pH 7.0, is radiolabelled using one mCi of $^{125}$I (Amersham Nuclear, Cambridge, Mass.) in a reaction catalyzed by exposure to 150 ug/ml chloramine-T for 30 seconds. The reaction is terminated by the addition of 20 ug of sodium bisulfite, and the reactants are diluted to a total volume of 0.5 ml with 0.05M sodium phosphate buffer, pH 7.4, containing 1% bovine serum albumin (hereinafter referred to as "buffer" ). Radiolabelled I-FABP is separated from free $^{125}$I by gel filtration using a Sephadex G-25 column (Pharmacia, Uppsala, Sweden) in buffer. Approximately 73% of the counts are eluted in a primary peak which contains I-FABP fractions. The front of this peak is collected separately. Eighty-five percent of the counts in this peak are precipitated by the addition of trichloracetic acid. The fraction is diluted in buffer to a concentration of 17,500 cpm/ul and stored at 4° C. In this state, the label remains stable for at least 6 weeks.

Antiserum Production. Polyclonal antibodies to recombinant rat I-FABP are produced in New Zealand white rabbits (Charles River, Cambridge, Mass.). Animals receive subcutaneous injections of 330 ug I-FABP in Freund's incomplete adjuvant. Animals are boosted in one month using 150 ug of I-FABP. Sera are screened using agarose immunoelectrophoresis.

Antiserum Specificity. Extracts of stomach, small intestine, colon, and liver, together with pure, recombinant I-FABP are subjected to electrophoresis in a 15% acrylamide gel. Protein from this gel is transferred to a PVDF transfer membrane (Millipore, Bedford, Mass.). The membrane is exposed to a 1:300 (v/v) dilution of rabbit anti-I-FABP and stained using an avidin-biotin system with diaminobenzidine. Western blot analysis shows a 15 kilodalton (kD) band in each lane, corresponding to the heavy band of monomeric, recombinant I-FABP. Secondary bands, representing lower molecular weight degradation products of I-FABP, are apparent in the lanes with extracts of stomach, jejunum, and ileum, but not in intestinal and liver tissue extracts. A light, 31 kD band, probably representing a protein dimer, is apparent in the lane containing recombinant I-FABP.

Antiserum Titer. One hundred ul of the tracer (about 17,500 cpm) are incubated overnight at 4° C. with 300 ul of a 1:2 dilution series of rabbit anti-rat I-FABP in buffer. Nonspecific binding is blocked by the addition of 100 ul of normal rabbit serum (1:200, v/v). Bound antibody is separated using a second antibody method with sheep anti-rabbit immunoglobulin (IgG). Following incubation for 8 hours at room temperature, the samples are centrifuged at 2500 rpm for 15 minutes, the supernatant discarded, and the pellets counted in a gamma counter (Beckman Instruments, Cambridge, Mass.).

Activity and Sensitivity of the Antiserum. A 2:1 (v/v) dilution series of I-FABP (1.9 to 250 ng/ml) in buffer (total volume is 100 ul/sample) is incubated with 100 ul of rabbit anti-rat I-FABP (1:8000, v/v) and 100 ul of tracer. All samples are analyzed in duplicate. Following an incubation at 4° C., antibody is precipitated using the second antibody method. The pellets are counted in a gamma counter, and a standard curve is constructed. A typical standard curve is presented in FIG. 1.

Figure 2:
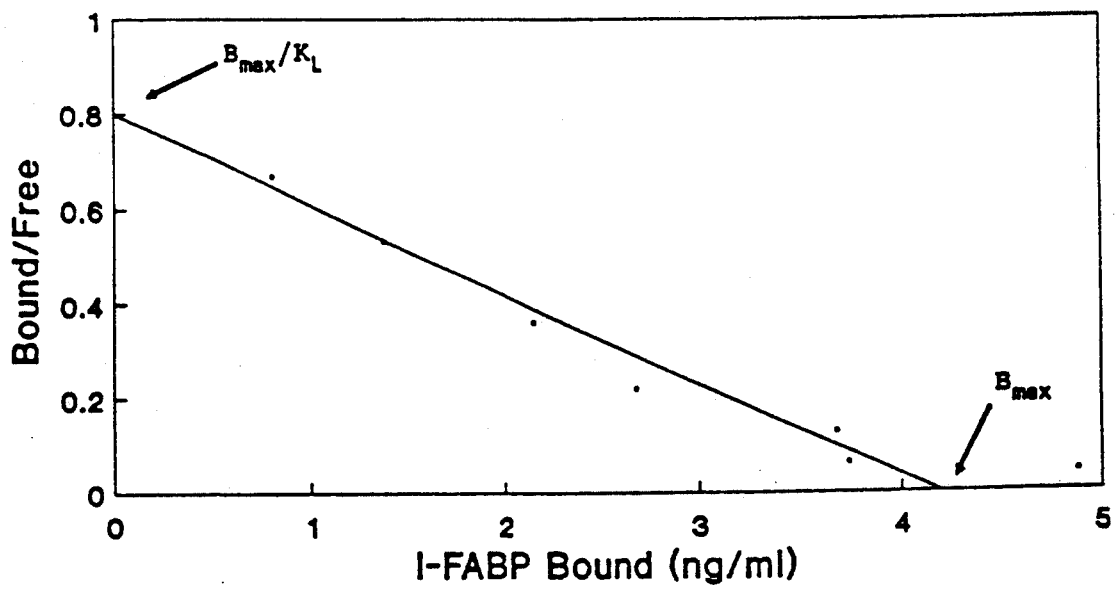
FIG. 2 is a Scatchard plot showing the proportion of I-FABP (1:8000, v/v) relative to free I-FABP versus concentration of bound I-FABP. The Y-intercept corresponds to $B_{max}/K_L$ and the X-intercept corresponds to $B_{max}$. The equilibrium dissociation constant for the I-FABP/antibody system, $K_L$, is $3.5 \times 10^{10}$ 1/mol.

Ninety percent of labelled tracer (17,500 cpm/100 ul) could be precipitated at a dilution of 1:250 (v/v). Sixty percent of the label is precipitated at a titer of 18000 (v/v), and this is then used as a working dilution. Scatchard analysis reveals that the dissociation constant, $K_L$, for this antiserum is about $3.5 \times 10^{10}$ 1/mol (FIG. 2). The standard curve constructed from 1.9 to 250 ng/ml becomes linear above 3.9 ng/ml, and this is defined as the lower limit of detection for the assay (FIG. 3).

I-FABP in Serum, Urine, and Tissues. Blood and urine are obtained from 250-400 gm LBN rats (Charles River, Cambridge, Mass.) on a standard diet. Following ether/phenobarbital anesthesia, blood is obtained by aortic cannulation, serum from several rats is pooled, and samples are frozen at −20° C. Urine is obtained by bladder puncture and centrifuged. Supernatants are similarly pooled and frozen. Tissues are obtained from stomach, small intestine, right colon, and liver under ether/phenobarbital anesthesia. The small intestine is divided into three segments: duodenum (pylorus to duodenojejunal flexure), jejunum (proximal one-half segment from duodenojejunal flexure to ileocecal valve) and ileum (remaining segment). Mucosa from the stomach and small intestines is removed and homogenized with a Teflon ™ pestle in a Potter-Elvenheim vessel in 2.5 volumes of 0.1M phosphate buffer, pH 7.4, at 4° C. The homogenate is cleared by centrifugation for 15 minutes at 800 g. The supernatants are collected and then centrifuged for one hour at 105,000 g. The supernatants are stored at −70° until they are analyzed.

Whole serum (n=10) and delipidated serum (n=5) are analyzed for I-FABP using radioimmunoassay. Delipidation is accomplished by the addition of two volumes of butanol and diethyl ether (40:60, v/v) to one volume of serum containing 0.1 mg/ml EDTA. Following rotation for 30 minutes and centrifugation, the aqueous layer is aspirted, mixed with two volumes of diethyl ether, and centrifuged. The aqueous layer is aspirated and residual ether removed by suction. Dilution series of serum, delipidated serum, and urine to which known amounts of pure I-FABP is added are analyzed and the respective curves compared to the standard curve prepared using pure I-FABP.

Figure 3:
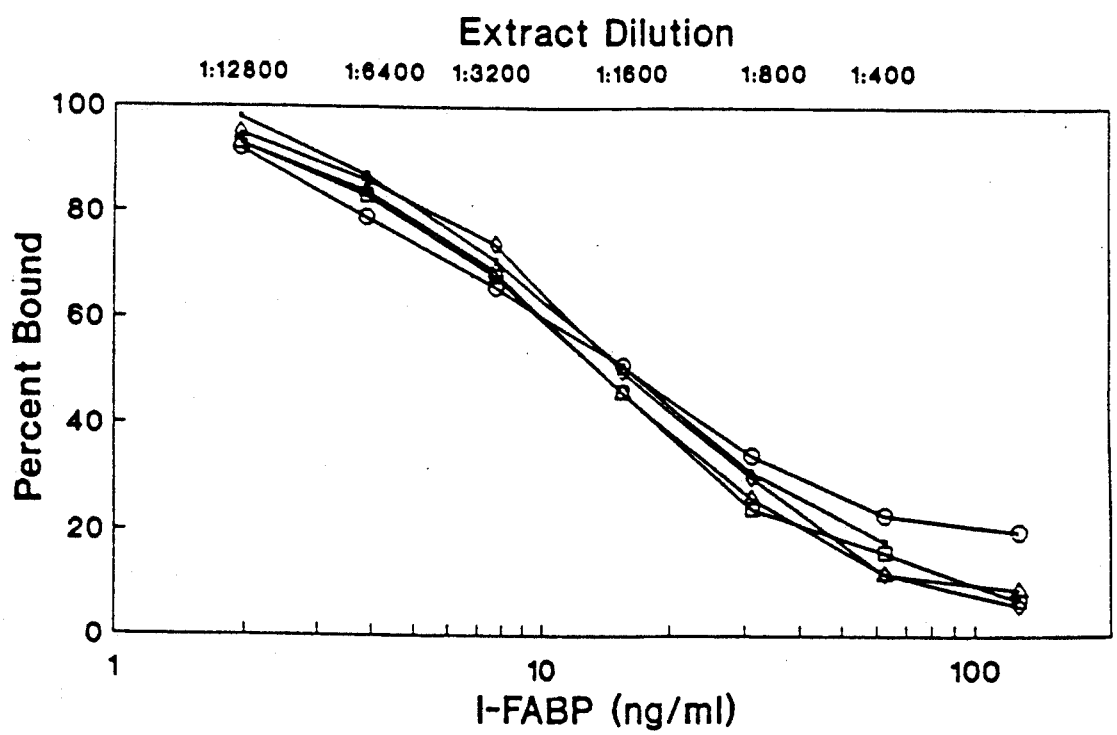
FIG. 3 shows serial dilutions of recombinant, rat I-FABP diluted with buffer (△), dilute serum (◊), dilute urine (□), and whole, delipidated serum (○); serial dilutions of a jejunal extract (•) are also plotted.

The results are plotted in FIG. 3. Dilution curves of whole serum, delipidated serum, and urine to which known amounts of I-FABP have been added and the dilution curve of a jejunal extract are parallel to the standard curve for pure, recombinant I-FABP. Although I-FABP is not detectable in native, undiluted serum of normal rats, it could be detected in delipidated sera in a concentration of $8.6 \pm 1.9$ ng/ml. Immunoreactive I-FABP is detected in the undiluted urine of 8 of 24 rats and ranged in concentration between 4.0 and 15.5 ng/ml.

I-FABP Content of Tissue Undiluted 100 ul samples of tissue homogenates, prepared as described above, are assayed for I-FABP content. I-FABP content is expressed both in relation to wet weight of tissue and total protein content. Protein content of the samples are determined as described by Bradford (Anal. Biochem. 72:248-254 (1976)).

The results are tabulated in Table 1 below.

TABLE 1

| Extracted Tissue | I-FABP (ng/mg wet wt.) | I-FABP (ng/mg protein) |
|---|---|---|
| Gastric mucosa | 7.0-8.9 | 624-889 |
| Duodenal mucosa | 25-115 | 1444-8846 |
| Jejunal mucosa | 31-152 | 2903-10427 |
| Meal mucosa | 26-130 | 1580-8830 |
| Colonic musosa | 3.5-4.2 | 741-1081 |
| Liver | 1.5-4.4 | 41-114 |

Extracts from the duodenum, jejunum, and ileum contain large amounts of I-FABP, while stomach, colon and liver contain small amounts of immunoreactive protein. The tissue concentrations are similar to those reported by others as determined by other methods (Bass, N. M., and Manning, J. A., Biochem. Biophys. Res. Commun. 137:929-935 (1986) and Gordon, J. I., and Gordon J. L. and Lowe, J. B., Chem. Phys. Lipids 38: 137-158 (1985)). While not wishing to be bound to any theory, the nearly three-fold variability in I-FABP content between animals for a given segment of a small intestine may be a diurnal variation like that observed in liver fatty acid binding protein levels by Dempsey, et al. (Chem. Phys. Lipids 38:223-237(1985)).

I-FABP Pharmacolinetics. Anesthetized LBN rats undergo celiotomy and isolation of the portal vein. Pure I-FABP (5 ug) is injected directly into the portal vein. Peripheral venous serum samples are obtained prior to and at various times following portal vein injection and analyzed using radioimmunoassay. Urine is also obtained before injection and at the conclusion of each experiment. An aliquot of serum obtained 5 minutes after portal infusion of 200 ug of pure I-FABP and an aliquot of urine obtained 90 minutes after the same infusion are gel filtered on a Sephadex G-50 (Pharmacia, Uppsala, Sweden) column (0.9×30 cm, 0.4 ml/fraction). A 400 ul sample of radiolabelled I-FABP (17.000 cpm/100 ul) is gel filtered in order to calibrate the column for use with the samples.

Figure 4:
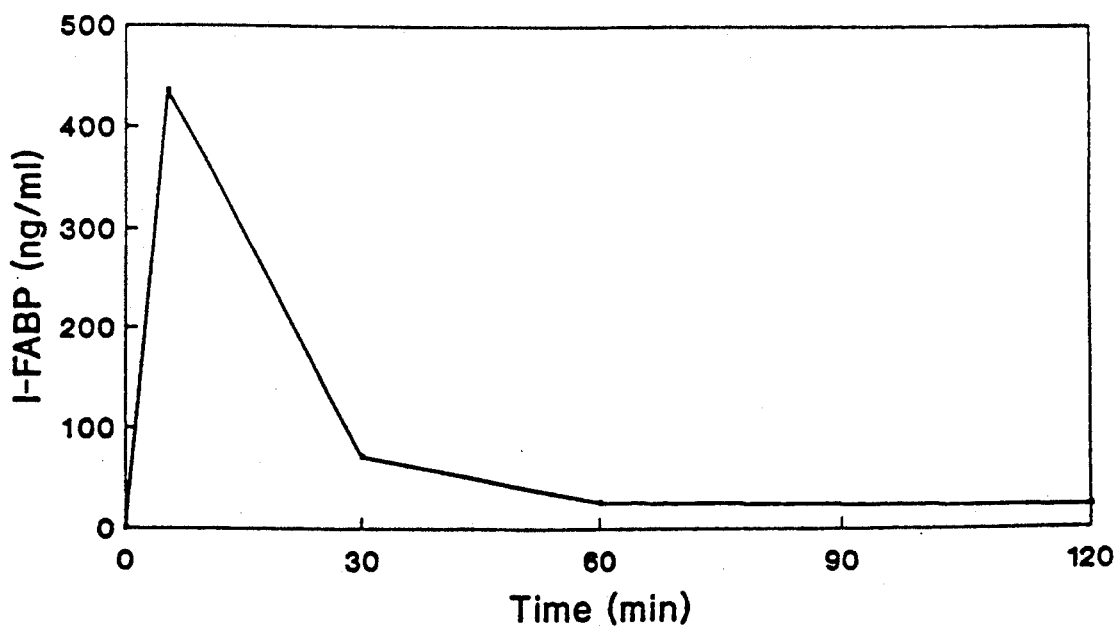
FIG. 4 plots I-FABP concentration in the peripheral circulation of a rat following portal vein injection of 10 ug of I-FABP. Peak concentrations of I-FABP are achieved within 10 minutes, and the protein is essentially cleared from the peripheral circulation with a $t_{\frac{1}{2}}$ of 20 minutes.

Following infusion of at least five micrograms of I-FABP into the portal vein, the protein could be detected in the peripheral circulation and in the urine. Serum levels plateaued after 30 minutes and remained detectable in diluted serum for more than four hours following the portal infusion of 10 ug of protein (FIG. 4).

Figure 5:
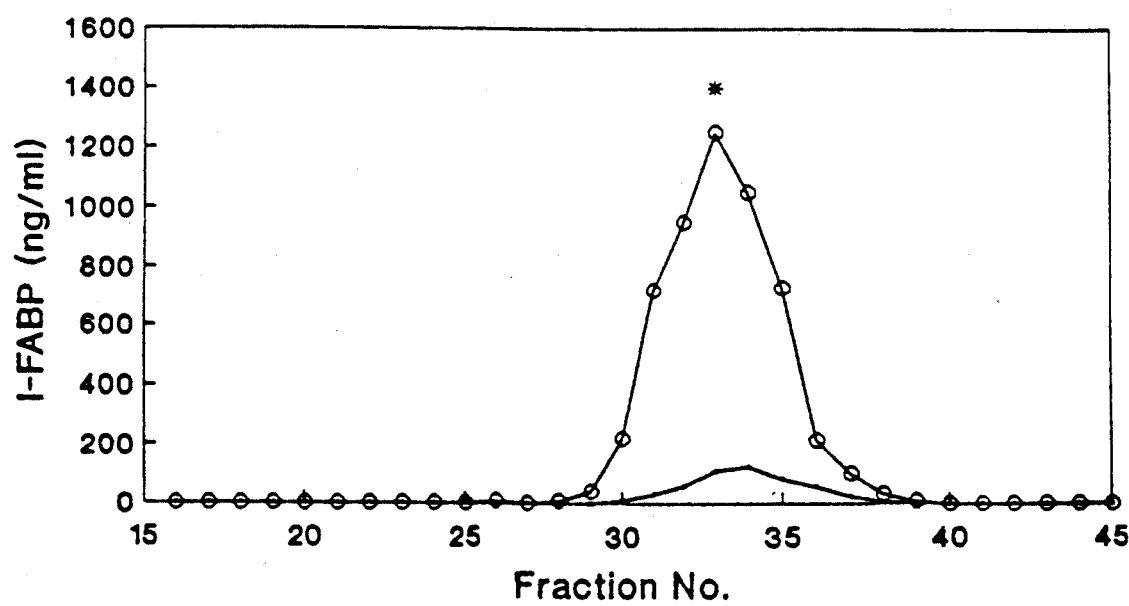
FIG. 5 is a gel filtration elution curve of biological samples containing I-FABP. After infusing two hundred micrograms of I-FABP into the portal circulation of a rat, peripheral serum collected 5 minutes after infusion (○) and urine collected 90 minutes after infusion (•) are gel filtered, with fractions analyzed for I-FABP by radioimmunoassay. A 400 ul aliquot of radiolabelled I-FABP is gel filtered as well, and total cpm in each fraction, determined. Peak activity is found in fraction number 34 (*).

The elution volumes for immunoreactive I-FABP are identical for radiolabelled, recombinant I-FABP and peripheral sera and urine obtained from animals after portal infusion of I-FABP, indicating that the assay is specific for I-FABP. Moreover, as has been discussed above, standard curves for I-FABP are also essentially parallel to dilution curves of intestinal extracts. No secondary immunoreactive peaks are identified (FIG. 5). This finding indicates that the immunoreactive I-FABP detected in the peripheral circulation and urine by the radioimmunoassay is native I-FABP and not a smaller, immunoreactive metabolite.

EXAMPLE 2

In this example, I-FABP is detected (using the assay described in Example 1 above) in the serum and urine of animals at an early stage of intestinal ischemic damage.

Male LBN rats weighing 250 to 350 grams are examined in two models of mesenteric ischemia. In group one (n=15), animals are subjected to 60 minutes of superior mesenteric artery occlusion. During the ensuing period of reperfusion, samples of portal and systemic blood and urine are obtained over five hours. In group two (n=10), the arterial supply, except for collaterals, to a 10 cm segment of jejunum is ligated. Samples of blood and urine are obtained over five hours.

The samples are analyzed for hexoseaminidase (hereafter abbreviated HEX) using the fluorimentric technique described by Lobe, et al., cited above. Briefly stated, serum is stabilized by acidifying and adding bovine serum albumin, and then substrate (4-methylumbelliferyl-N-acetyl-beta-O-glucosaminide) and buffer are added and the samples incubated and fluorescence read with a spectrofluorimeter. The samples are also analyzed for I-FABP as described in Example 1. Biopsy specimens are obtained at the end of each experiment.

The results are presented in Table 2.

the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. A method for screening for the presence or absence of a pathologic condition in the intestinal tract of an animal or a human being which comprises:
   (a) obtaining a biological sample from said animal or human being;
   (b) determining the level of intestinal fatty acid binding protein in said sample;
   (c) comparing said determined level of intestinal fatty acid binding protein to the level of intestinal fatty acid binding protein in a corresponding normal biological sample; and
   (d) determining the presence of said pathologic condition by observation of whether said determined level exceeds said normal level.

2. A method according to claim 1 wherein said biological sample is selected from the group consisting of serum, urine, and a tissue homogenate prepared from an intestinal biopsy obtained from said animal or human being.

3. A method according to claim 2 wherein said biological sample is serum or urine.

4. A method according to claim 2 wherein the pathologic condition is selected from the group consisting of

TABLE 2

Serum and urine I-FABP (ng/ml) and serum hexosaminidase (nM/l) values prior to and at intervals to 300 minutes following 60 minutes of SMA occlusion (Group 1) or ligation of arterial supply to a 10 cm segment of jejunum (Group 2).

| Group 1 | Time from Onset of Reperfusion | | | | | | |
|---|---|---|---|---|---|---|---|
| | Baseline | 0 min. | 15 min. | 30 min. | 60 min. | 90 min. | 300 min. |
| Peripheral I-FABP | <4.0 | 7.9 ± 7.6 | 44.2 ± 10.0 | 41.9 ± 13.1 | 55.6 ± 10.5 | 129.8 ± 37.2 | 77.8 ± 38.7 |
| Portal I-FABP | <4.0 | 49.2 ± 19.9 | 90.3 ± 24.3 | 70.8 ± 20.8 | 80.3 ± 18.2 | 183.8 ± 55.2 | — |
| Urine I-FABP | <4.0 | — | — | — | 8.4 ± 0.0 | 11.0 ± 0.0 | 68.0 ± 0.0 |
| Peripheral HEX | 486 ± 78 | 398 ± 65 | — | — | 304 ± 55.2 | 457 ± 106 | 392 ± 62 |

| Group 2 | Time from Arterial Ligation | | | | | | |
|---|---|---|---|---|---|---|---|
| | Baseline | 15 min. | 60 min. | 120 min. | 180 min. | 240 min. | 300 min. |
| Peripheral I-FABP | <4.0 | 8.5 ± 4.7 | 4.6 ± 4.4 | 18.2 ± 7.4 | 30.3 ± 11.1 | 51.2 ± 20.7 | 38.2 ± 18.0 |
| Urine I-FABP | <4.0 | — | — | — | — | 22.5 ± 6.0 | 51.2 ± 14.8 |
| Peripheral HEX | 438 ± 54 | 414 ± 68 | 452 ± 31 | 467 ± 56 | 403 ± 65 | 454 ± 68 | 424 ± 86 |

Baseline serum I-FABP is below 4 ng/ml (the limit of detection for the assay) in the portal and systemic circulation of all animals. Baseline urine I-FABP is detected in 13 of 25 animals, with a mean of 8.1±0.9 ng/ml. In group 1, I-FABP rises immediately upon reperfusion and peaks at 90 minutes in the portal and systemic circulations. In group two, serum I-FABP rises steadily over the baseline beginning 15 minutes after ligation. Elevation of urine I-FABP is significant in both groups after 60 minutes. In neither model is there a significant change in serum hexoseaminidase. Histologic specimens obtained at the conclusion of each experiment are remarkagle only for mild to moderate mucosal injury.

Thus, immunoreactive I-FABP rises significantly in both serum and urine of rats with moderate ischemic damage to the intestinal mucosa. I-FABP became significantly elevated in the peripheral circulation within minutes of the onset of a clinically-relevant ischemic insult.

The above description is for the purpose of teaching the person of ordinary skill in the art how to practice intestinal ischemia, necrotizing enterocolitis, inflammatory bowel disease, and bowel graft rejection.

5. A method according to claim 4 wherein the pathologic condition is intestinal ischemia.

6. A method according to claim 2 wherein an immunological assay selected from the group consisting of a radioimmunoassay and an enzyme-linked immunosorbent assay is employed to determine said levels of intestinal fatty acid binding protein.

7. A method according to claim 6 wherein said immunological assay employs antibody to rat intestinal fatty acid binding protein.

8. A method according to claim 7 wherein said antibody is polyclonal.

9. A method according to claim 7 wherein said rat intestinal fatty acid binding protein is recombinant rat intestinal fatty acid binding protein.

10. A method for screening for intestinal ischemia in an animal or a human being which comprises detecting elevated intestinal fatty acid binding protein in a serum or urine sample obtained from said animal or human being.

11. A method according to claim 10 wherein said detecting employs a radioimmunoassay or an enzymeimmunoassay.

12. A method using according to claim 11 wherein said radioimmunoassay employs a rabbit polyclonal antibody to rat intestinal fatty acid binding protein.

13. A method according to claim 12 wherein the equilibrium dissociation constant for the intestinal fatty acid binding protein/antibody system is about $3.5 \times 10^{10}$ l/mol.

14. A method according to claim 12 wherein said intestinal fatty acid binding protein is a recombinant rat intestinal fatty acid binding protein.

15. A method according to claim 12 wherein said radioimmunoassay is sensitive to immunoreactive intestinal fatty acid binding protein concentrations between about 4 and about 125 ng/ml.

16. A method according to claim 10 wherein said sample is a serum sample.

17. A method for screening for the presence of intestinal ischemia in an animal or a human being which comprises:
(a) obtaining a urine or serum sample from said animal or human being;
(b) assaying for the level of intestinal fatty acid binding protein in said sample; and,
(c) comparing said level of intestinal fatty acid binding protein to the level of intestinal fatty acid binding protein in a corresponding normal sample; and
(d) determining the presence of ischemia by observation of whether said level exceeds said normal level.

18. A method according to claim 17 wherein the level of intestinal fatty acid binding protein is determined using an immunological assay. fatty acid binding protein is recombinant rat fatty acid binding protein.

19. A method for screening for the presence of a pathological condition in a patient's intestinal tract selected from the group consisting of intestinal ischemia, necrotizing enterocolitis, inflammatory bowel disease, and bowel graft rejection, which comprises:
(a) obtaining a serum or urine specimen from the patient;
(b) assaying for the presence, if any, of intestinal fatty acid binding protein in the specimen; and
(c) determining the presence of said pathological condition by observation of whether said determined level exceeds the level in a normal patient.

20. A method according to claim 19 wherein said assay for intestinal fatty acid binding protein is an immunological assay.

* * * * *